Figure 1:
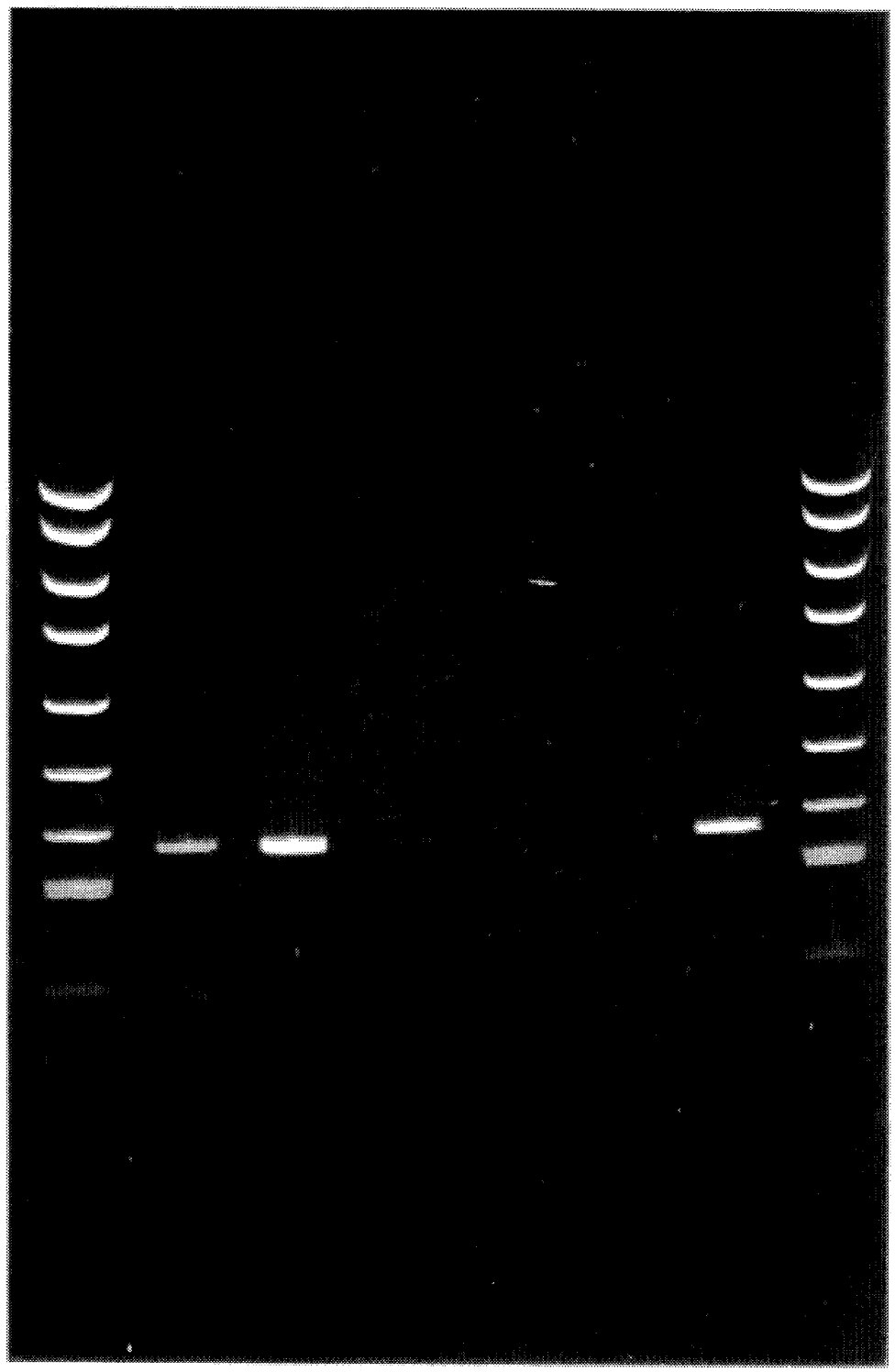

United States Patent [19]
Mueller et al.

[11] Patent Number: 5,503,981
[45] Date of Patent: Apr. 2, 1996

[54] ISOLATION OF FETAL CELLS FROM MATERNAL BLOOD TO ENABLE PRENATAL DIAGNOSIS

[75] Inventors: Utz W. Mueller, Torens Park; Catherine S. Hawes, Fullarton, both of Australia

[73] Assignee: Flinders Technologies Pty, Ltd., Australia

[21] Appl. No.: 700,139

[22] PCT Filed: Nov. 29, 1989

[86] PCT No.: PCT/AU89/00517

§ 371 Date: Jul. 3, 1991

§ 102(e) Date: Jul. 3, 1991

[87] PCT Pub. No.: WO90/06509

PCT Pub. Date: Jun. 14, 1990

[30] Foreign Application Priority Data

Dec. 6, 1988 [AU] Australia ............................. PJ1824/88

[51] Int. Cl.$^6$ .................................................. G01N 33/567
[52] U.S. Cl. .................. 435/7.21; 435/7.92; 435/70.21; 435/240.27; 435/968; 436/526; 436/548; 530/388.2
[58] Field of Search ....................... 436/536, 548, 436/65, 518, 526; 530/403, 387.9, 388.1, 388.15, 388.7, 388.85, 388.2; 435/7.92, 7.21, 70.21, 240.27, 968

[56] References Cited

FOREIGN PATENT DOCUMENTS 0430402 6/1991 European Pat. Off. .

OTHER PUBLICATIONS

Mueller et al., "Isolation of Fetal Trophoblast Cells from Peripheral Blood of Pregnant Women", *The Lancet*, vol. 336, pp.197–200, (1990).
Parks et al., "Fetal Cells from Maternal Blood: Their Selection and Prospects for Use in Prenatal Diagnosis", in*Methods in Cell Biology,*, vol. 26, Academic Press, Inc., pp. 277–295 (1982).
Mueller et al., "Identification of Extra–villous Trophoblast Cells in Human Decidua using an Apparently Unique Murine Monoclonal Antibody to Trophoblast", *Hisotchemical Journal*, vol. 19, pp. 288–296 (1987).
Nickson et al., "Molecular Cloning and Expression of Human Trophoblast Antigen FD0161G and Its Identification as 3β–hydroxy–5–ene Steroid Dehydrogenase", *J. Reprod. Fert.*, vol. 93, pp. 149–156 (1991).
Molday et al., Separation of Cells Labeled with Immunospecific Iron Dextran Microsheres Using High Gradient Magnetic Chromatography, vol. 170, No. 2, pp. 323–238 (1984).
Pourfarzaneh et al., "The Use of Magnetizable Particles in Solid Phase Immunoassay", in *Methods of Biochemical Analysis*, D. Glick, ed., John Wiley, New York, vol. 28, pp. 267–295, (1981).
Mueller, U. W., Histochemical Journal 19, 288–296 (1987).
Sen–Majumdar, A., Biochemistry 25, 634–640 (1986).
Chemical Abstracts 103:192486c.
Chemical Abstracts 104:82124w.
Chemical Abstracts 102:44039y.
Butterworth et al—Chem. Abst. vol. 103 (1985) p. 192,486c.
Kawata et al—Chem. Abst. vol. 101 (1984) p. 149,452k.
Biological Abstracts, vol. 73, 47702 (1982).
Biological Abstracts, vol. 84, 71902 (1987).
Biological Abstracts, vol. 87, 35303 (1989).
Biological Abstracts, vol. 87, 35304 (1989).
Chemical Abstracts, 105:40798j (1986).

*Primary Examiner*—Carol A. Spiegel
*Assistant Examiner*—Susan C. Wolski
*Attorney, Agent, or Firm*—Birch, Stewart, Kolasch & Birch

[57] ABSTRACT

This invention relates to a method for the isolation of trophoblast (placental) cells from the blood of a pregnant mammal so as to provide the essential starting material, namely cells derived from the fetus, to enable genetic and/or biochemical information about the fetus to be obtained. In particular, this invention relates to the use of monoclonal antibodies specific for membrane protein markers on mammalian trophoblasts to isolate trophoblast cells from maternal blood. These cells may then be used to obtain fetal genetic and/or biochemical information early in pregnancy. The present invention is particularly relevant for detecting human fetal abnormalities.

12 Claims, 1 Drawing Sheet

ISOLATION OF FETAL CELLS FROM MATERNAL BLOOD TO ENABLE PRENATAL DIAGNOSIS

This invention relates to a method for the isolation of trophoblast (placental) cells from the blood of a pregnant mammal so as to provide the essential starting material, namely cells derived from the fetus, to enable genetic and/or biochemical information about the fetus to be obtained. In particular, this invention relates to the use of monoclonal antibodies specific for membrane protein markers on mammalian trophoblasts to isolate trophoblast cells from maternal blood. These cells may then be used to obtain fetal genetic and/or biochemical information early in pregnancy. The present invention is particularly relevant for detecting human fetal abnormalities.

Currently, prenatal testing is carried out on fetal cells obtained by either amniocentesis or chorionic villous sampling (CVS). Amniocentesis is normally performed around 16 weeks of gestation. The procedure involves attendance by skilled personnel to insert a needle into the amniotic sac of the fetus and remove between 20–30 ml of amniotic fluid. The amniotic fluid contains fetal cells to allow subsequent tests to be performed. This method of obtaining fetal cells is associated with a risk of inducing a spontaneous abortion. In addition, if the subsequent genetic diagnosis of the fetus reveals an abnormality, the prospect of a mid-trimester pregnancy termination is both psychologically stressful and associated with some physical risk to the mother.

Chorionic villus sampling also requires the involvement of skilled personnel to take a small biopsy from the placenta of an 8–12 week old fetus. Again this procedure has some risk of inducing a spontaneous abortion, although the early diagnosis of any chromosomal abnormality makes the procedure more attractive than amniocentesis. However, the need for skilled personnel and the possibility of inducing spontaneous abortion for both procedures means that current prenatal genetic assessments are made only on pregnant women who are deemed "at risk" of carrying a chromosomally defective fetus.

The method of the present invention provides a simpler procedure which involves obtaining blood from an arm vein of a pregnant mammal such as a pregnant woman and extracting fetal cells which are normally sloughed off from the placenta into the maternal circulation. No specialised expertise is required to obtain this blood sample and this non-invasive isolation of fetal cells negates any risk of inducing a spontaneous abortion. The blood may be taken around the same gestational time as for chorionic villus sampling hence the benefits of early diagnosis are gained.

Although the presence of trophoblast cells in maternal peripheral blood has been the subject of some debate, Goodfellow and Taylor (1982) have reported the extraction of trophoblast cells circulating in peripheral blood during pregnancy by use of differential centrifugation. Covone et al (1984) investigated the possibility of detecting trophoblast cells in the peripheral blood from women at various stages of gestation by the use of monoclonal antibody H315 (Johnson et al, 1981), however in subsequent reports (Pool et al, 1987; Adinolfi et al, 1989), it was suggested that the isolation of H315-positive cells as a source of diagnostic material for antenatal diagnosis of fetal abnormalities is impractical. Recent data suggests that the frequency of fetal cells in the maternal circulation (from 12 weeks to 36 weeks gestation) is less than 1 in 100,000 (Adinolfi et al, 1989; Schwinger et al, 1989).

According to one aspect of the present invention, there is provided a method for the isolation of trophoblast cells from a blood sample of a pregnant mammal which method comprises contacting said blood sample with a binding-effective amount of an antibody specific for villous syncytiotrophoblast and non-villous cytotrophoblast cells for a time and under conditions sufficient for said antibody to bind to target cells and then separating said cells bound by said antibody from said sample.

Another aspect of the present invention is directed to a method for obtaining fetal genetic and/or biochemical information in a pregnant mammal which method comprises isolating a blood sample from said pregnant mammal and contacting said blood sample with a binding-effective amount of an antibody specific for villous syncytiotrophoblast and non-villous cytotrophoblast cells for a time and under conditions sufficient for said antibody to bind to said cells and then separating cells bound by said antibody from said sample and obtaining from the isolated cells genetic and/or biochemical information.

Yet another aspect of the present invention relates to a kit for the isolation of trophoblast cells from a blood sample of a pregnant mammal and optionally for obtaining genetic and/or biochemical information about said cells comprising in compartmental form a first container adapted to contain an antibody specific for villous syncytiotrophoblast and non-villous cytotrophoblast cells; optionally a second container adapted to receive and contain a blood sample from said pregnant mammal; and optionally a third container adapted to contain a means for obtaining from the isolated cells genetic and/or biochemical information.

In a preferred embodiment of the present invention, the mammal is a pregnant human female and one or more of the antibodies FDO161G or FDO66Q or FDO338P is/are used.

Still yet another aspect of the present invention relates to the homogeneous or near homogeneous antigens, FDO161G or FDO66Q protein and FDO338P protein, or their derivatives.

The present invention is further described with reference to FIG. 1. This figure is a photographic representation of an analysis of products from PCR of trophoblast cells isolated from peripheral blood of pregnant women. Analysis was performed in a 15% (w/v) polyacrylamide gel. Tracks 1 & 8: DNA size markers, (pUC19/Hpa II digest; Top-button 501, 489, 404, 331, 242, 190, 147, 111, 110, 67, 34 bp); tracks 2 & 3: trophoblast cells isolated from blood of two individual women carrying a male fetus; tracks 4 & 5: trophoblast cells isolated from the blood of two individual women carrying a female fetus; track 6: no DNA blank; rack 7: control trophoblast cells derived from a full-term placenta of a male child.

The present invention is directed to a method for isolating trophoblast (placental) cells from a blood sample of a pregnant mammal. The trophoblast cells so isolated are a convenient source of genetic and/or biochemical material from which fetal analysis can occur such as for potential fetal abnormality. The isolation of trophoblast cells is predicated on the use of antibodies, and in particular monoclonal antibodies, although not necessarily limited thereto, specific for villous syncytiotrophoblast and non-villous cytotrophoblast cells. Accordingly, in one aspect of the present invention there is provided a method for the isolation of trophoblast cells from a blood sample of a pregnant mammal which method comprises contacting said blood sample with a binding effective amount of an antibody specific for villous syncytiotrophoblast and non-villous cytotrophoblast cells for a time and under conditions sufficient for said antibody to bind to cells and then separating cells bound by said antibody.

For the purpose of exemplification only, the present invention is described using blood from a pregnant human female to isolate human placental cells. This is done, however, with the understanding that the present invention extends to all mammals. In extending to mammals other than humans, it may be necessary to alter the specificity of the trophoblast binding antibodies. The present invention, therefore, extends to all such antibodies as well as those, described herein, specific for human villous syncytiotrophoblast and non-villous cyotrophoblast cells.

By "binding effective amount of antibody" as used in the specification and claims herein is meant an amount of antibody sufficient to bind to the target cells and be used in the isolation of such cells. It is a preferred embodiment of the subject invention that the antibodies be coupled to a substrate such as magnetic polystyrene beads precoated with sheep anti-mouse IgG (Fc fragment) serum (Dynabeads M-450, Dynal AS, Oslo, Norway). However, other substrates could be used such as a fluorescent chemical. The blood sample is contacted with an effective amount of beads, i..e. from about 2000 to 10,000 beads/ml of whole blood and preferably about 4000 beads/ml (i.e. about $10^5$ beads per 25 ml sample) and allowed to incubate at 4° C. overnight. The beads with trophoblast cells attached via the specific trophoblast reactive antibody are removed using the cobalt-samarium magnet (Dynal AS). These methods represent an optimal protocol in terms of performance and/or convenience but may be subject to variations to suit the particular situation but which are still within the scope of the present invention which contemplates all such variations.

Accordingly, the present invention relates to a method for the isolation of trophoblast cells from a blood sample from a pregnant woman, which comprises contacting the blood sample with an antibody specific for villous syncytiotrophoblast and non-villous cytotrophoblast cells, and subsequently separating cells bound by said antibody from said sample.

The fetal trophoblast cells so isolated from the maternal blood sample can then be assessed for their genetic and/or biochemical characteristics using known diagnostic techniques.

Either monoclonal or polyclonal antibodies may be used or combinations thereof for the step of separating trophoblast cells from the blood sample, however the use of a monoclonal antibody is preferred.

In a particularly preferred aspect of this invention, three antibodies have been used for the isolation of trophoblast cells. They are designated FDO161G (Mueller et el, 1987), FDO66Q an FDO338P.

These antibodies are each a mouse monoclonal antibody secreted by an individual hybridoma cell line which grows indefinitely in tissue culture and can be stored frozen in liquid nitrogen. Further details of these monoclonal antibodies and the production thereof are provided herein. Each of these three monoclonal antibodies are of the heavy chain subclass, $G_i$ and light chain, kappa. Other sources of monoclonal antibodies are encompassed by the present invention.

The monoclonal antibodies FDO161G and FDO66Q have apparent specificity for the same, or a closely associated epitope of a trophoblast membrane protein (hereinafter referred to as the "FDO161G/FDO66Q protein, or antigen") which resides on villous syncytiotrophoblast and non-villous cytotrophoblast cells of human first trimester and term placentas and invading non-villous cytotrophoblast cells in human decidua.

The protein has not been detected on villous cytotrophoblast cells using either the FDO161G or the FDO66Q antibody. It was detected on a restricted number of other human tissues, viz. thecal and granulosa cells of mature ovarian follicles, interstitial cells of testis and cells in the zona fasciculata/glomerulosa of adrenal cortex, but it was not detected on a wide range of other human tissues and cells, including peripheral blood cells and villous mesenchyma. These results are presented in Tables 1 & 2. The epitope of the membrane protein recognised by the FDO161G antibody (and the same, or closely associated epitope recognised by FDO66Q) was, however, detected on baboon and marmoset placentas. It was also present on cultured human first trimester trophoblast cells and a human choriocarcinoma line, JEG-3.

TABLE 1

MONOCLONAL ANTIBODY REACTIVITY ON HUMAN TISSUES

| Mab clone: | FDO161G (FDO66Q) | FDO338P (FDO78/93P) |
|---|---|---|
| Tissue: | | |
| 6–12 wk Placenta | +++ | +++ |
| Term Placenta | ++ | ++ |
| Decidua | − | − |
| Endometrium (prolifertive) | − | − |
| Myometrium | − | − |
| Ovary | +[1] | − |
| Testis | +[2] | − |
| Kidney | − | − |
| Liver | − | − |
| Spleen | − | − |
| Liver | − | − |
| Lung | − | − |
| Adrenal | +[3] | − |
| Pancreas | − | − |
| Skin | − | − |
| Striated Muscle | − | − |
| Thyroid | − | − |
| Pituitary | − | − |
| Stomach | − | − |
| Rectum | − | − |
| Colon | − | − |

Notes:
[1]Reactive with thecal cells in mature follicles and the corpus luteum.
[2]Reactive with interstitial cells.
[3]Reactive with cortex cells (zona fasciculata/glomerulosa).

TABLE 2

MONOCLONAL ANTIBODY REACTIVITY ON HUMAN CELL SUSPENSIONS

| Cells: | Mononuclear Leukocytes | Granulocytes | T-ALL[1] | Granulosa Cells |
|---|---|---|---|---|
| Mab clone: | | | | |
| FDO161G (FDO66Q) | − | − | − | +++ |
| FDO338P (FDO78P) (FDO93P) | − | − | NT | − |
| FDO81C[2] | +++ | +++ | +++ | +++ |

Notes:
NT Not tested.
[1]T-acute lymphatic leukemia (JM-Line).
[2]FDO81C reacts with all cells. Used as positive control.

The monoclonal antibody, FDO338P, detects an epitope of a protein ("FDO338P protein or antigen") which resides on the human trophoblast membrane. This epitope is expressed on villous syncytiotrophoblast of human first trimester and term placentas. The epitope was also present on invading, non-villous cytotrophoblast cells of human decidua but at much lower density. It was not detected on villous cytotrophoblast cells of human placentas or on villous mesenchyma. The epitope of this membrane protein recognised by the FDO338P antibody was not detected on a wide range of other human tissues and cells including peripheral blood cells and serum components. These results are presented in Tables 1 & 2. Although the epitope defined by FDO338P was not detected on baboon or marmoset trophoblast, a related glycoprotein analogue is present. This analogue can be identified by other monoclonal antibodies produced in the inventors' laboratory, viz. FDO78P & FDO93P, which are directed to other epitopes on the human FDO338P antigen.

The cell and tissue distribution of the trophoblast membrane proteins detected by FDO161G or FDO66Q monoclonal antibodies, and FDO338P or FDO78P or FDO93P monoclonal antibodies are distinct from each other and from all other trophoblast antigens previously described.

Thus the monoclonal antibodies described by Johnson et al (1981) which react with syncytiotrophoblast also recognise decidual glands (H315) or lymphocytes (H316). The antibody NDOG1 (Sunderland et al, 1981) binds syncytiotrophoblast and cytotrophoblast and recognises a carbohydrate epitope. Trop. 1 and Trop. 2, described by Lipinski et al (1981) bind both syncytiotrophoblast and villous cytotrophoblast. The monoclonal antibody described by Loke and Day (1984) binds villous cytotrophoblast and endometrial glands (Anderson et al 1987). Monoclonal antibodies FDO161G, FDO66Q and FDO338P are all distinct when compared with the specificities of antibodies submitted to a World Health Organisation-sponsored Workshop held in 1986 (Anderson et el, 1987).

Accordingly, in a preferred aspect of this invention, the method for isolation of trophoblast cells comprises contacting the maternal blood sample with an antibody, preferably a monoclonal antibody, specific for an epitope(s) of trophoblast membrane protein(s) and subsequently separating cells bound by said antibody(ies) from said sample. One of three monoclonal antibodies is preferred, viz. the antibodies FDO161G and FDO66Q, which bind to epitope(s) of a membrane protein antigen residing on villous syncytiotrophoblast and non-villous cytotrophoblast cells and the antibody FDO338P which binds to an epitope of a different membrane protein antigen residing on villous syncytiotrophoblast and to a lesser extent, on non-villous cytotrophoblast cells. Thus these antibodies produced in the inventors' laboratory are specific for two distinct membrane protein antigens, FDO161G/FDO66Q protein and FDO338P protein, described in detail below. Furthermore, it is within the scope of the present invention to include the use of more than one antibody in combination. Hence, one or more antibodies may be employed.

The protein antigens detected by the monoclonal antibodies FDO161G or FDO66Q and FDO338P have been prepared from human term placentas. The placental tissue is solubilised using a detergent (CHAPS) to release individual membrane proteins. Agarose (Sepharose) beads with either FDO161G or FDO66Q or the FDO338 antibody covalently attached are then added to the mixture. After suitable incubation the beads are recovered and respective antigen which is bound to the monoclonal antibody, is then dissociated from the antibody using an acid solution The FDO161G/FDO66Q protein has been isolated from detergent-solubilised human term trophoblast membranes using affinity gel chromatography. It migrates as a single entity on sodium dodecyl-sulphate polyacrylamide gel electrophoresis having a molecular weight of 43 kiloDalton (kDa) for the dithiothreitol reduced protein. The unreduced protein migrates at a similar molecular weight indicating that the protein is not composed of polypeptide subunits. The protein was detected on the surface of cultured trophoblast cells by immunochemical analysis and on human ovarian granulosa cells by fluorescence analysis, indicating that it is a glycosylated protein.

The nature of the carbohydrate linkages to the polypeptide backbone of the FDO161G/FDO66Q protein was determined using a combination of enzymatic and chemical cleavage. Using endoglycosidase F, an enzyme which cleaves high mannose, hybrid and complex glycans adjacent to the amino acid, asparagine (i.e. all N-linked carbohydrate), no reduction in molecular weight was observed. This indicates that the FDO161G/FDO66Q protein contains no N-linked glycans. Using Trifluoromethanesulphonic acid, a chemical which cleaves both N- and O-linked glycans from the polypeptide backbone, a significant reduction in molecular weight (from 43 kDa to 31 kDa) was observed. This indicates that the FDO161G/FDO66Q protein contains only O-linked glycans (i.e. linked to either serine or threonine). Since each chain of oligosaccharide accounts for an approximate molecular weight difference of between 2000–4000 Da, it may be estimated that the FDO161G/FDO66Q protein has between 3–6 oligosaccharide chains per molecule.

Amino acid sequencing of this protein antigen was performed by standard methods on both the N-terminus of the molecule and an internal segment. The latter was derived after proteolytic digestion with Protease V8 (from *Staphylococcus aureus* V8) in phosphate buffer. This serine protease cleaves on the carbonyl side of Glu and Asp residues under these conditions. The amino acid sequences were determined using an automated gas-phase sequenator and conventional Edman degradation chemistry. The following sequences were obtained:

N-Terminal Sequence of the FDO161G/FDO66Q protein
Thr[1]-Gly-Trp-Ser-His-Leu-Val-Thr-Gly-Ala[10]-]-Gly-Gly-Phe-Leu-Gly-Gln-(Arg)-Ile-(Ile)-(Arg)[20]-Leu-(Leu)-Val-Lys-Lys[25].

Internal Sequence was obtained from Protease V8 digest of FDO161G/FDO66Q protein
-Phe[1]-(X)-Leu-Arg-Leu-Glu-Ser-Arg-(X)-Ser[10]-Phe-PrO-Leu-(Ser)-(X)-Met-Tyr-(X)-Ile[19].

Assignments were considered unambiguous unless in round parentheses (hereinafter designated Y). The assignments marked (X) indicate that no amino acid was released and may possibly be O-linked glycosylation sites (i.e. amino acid may either be Ser or Thr).

Both of the above sequences have been compared with the following Data bases: NBRF Standard Data Base; NBRF Auxiliary Data Base; Kyoto Data Base; Swiss Data Base; Newat Data Base (Total: 4525 sequences—1,116,976 amino acid residues). A correlation coefficient was set at 0.75. Only two proteins from the data bases exceeded this level, i.e. Paper Wasp (*Polistes jadwigae*) for the N-terminal sequence and Alpha-2u-globulin precursor from mouse for the internal, Protease V8 digest, fragment. Since the correlation coefficients were only 0.764 (over 14 amino acids) and 0.779 (over 9 amino acids) respectively, it may be concluded that the protein defined by FDO161G or FDO66Q monoclonal antibodies has not previously been sequenced.

On SDS-polyacrylamide gel electrophoresis, the FDO338P antigen prepared by affinity chromatography (as described above) migrates as a series of molecular weight entities ranging from above 30 kDa through to the largest, 67 kDa. The same bands are seen under both reducing and non-reducing conditions, indicating that the protein does not possess either inter- or intrachain disulphide bonds. The two largest and most abundant species, namely, the 63 and 67 kDa bands have been isolated to apparent homogeneity by electro-elution from the SDS-polyacrylamide gel. The protein eluted from FDO338P gel was shown to contain carbohydrate residues. The carbohydrate was removed with Trifluoromethanesulphonic acid, resulting in reduction of molecular weight of the protein to 30 kDa. Assuming that each oligosaccharide chain contributes between 2000–4000 Da to the apparent molecular weight on SDS-PAGE gels, it is estimated that the FDO338P glycoprotein has between 8–16 oligosaccharide chains. The nature of the oligosaccharide linkage to the polypeptide chain was investigated using endoglycosidases F and H. Endoglycosidase F cleaves both complex and high mannose N-linked (i.e. to asparagine residues), but not O-linked (i.e. to serine/threonine residues) oligosaccharides. Cleavage with this enzyme reduced the molecular weights of the two major bands from 63 and 67 kDa to 43 and 48 kDa respectively. Endoglycosidase H cleaves only high mannose-type N-linked oligosaccharides. No reduction in molecular weight was seen after treatment with this enzyme indicating an absence of high mannose chains. Thus the FDO338P glycoprotein appears to have between 3–6 O-linked oligosaccharide chains and 5–10 complex N-linked oligosaccharide chains.

Accordingly, the present invention extends to homogeneous or near homogeneous FDO161G/FDO66Q protein and FDO338P protein and/or their derivatives. By derivatives is meant any alteration such as addition, deletion and/or substitution to the amino acid and/or carbohydrate sequence or components of said proteins and extends to proteins or parts thereof associated with various molecules (e.g. lipids, other proteins etc.). All such proteins are encompassed by the present invention together with any antibodies, monoclonal or polyclonal, made thereto. By "homogeneous or near homogeneous" is meant a preparation at least 70% pure relation to other protein and preferably greater than 80%–90% pure.

The isolation procedure for the fetal trophoblast cells in the blood sample in accordance with the present invention may involve, for example, the use of murine monoclonal antibody FDO161G or FDO66Q or FDO338P coupled to a substrate such as magnetic beads. One such substrate which is commercially available and which has been found to be effective comprises uniform, magnetic polystyrene beads with affinity purified sheep anti-mouse $IgG_1$ covalently bound to the surface. Each monoclonal antibody (MAb) is secreted by an individual hybrid cell line which was produced by fusing mouse myeloma cell (P3X63-Ag8–653) with a mouse spleen cell producing the antibody. The individual hybrid cell lines of interest were thus immortalised. On growing in culture, each cell line secretes the respective MAb into the culture medium which can then be collected and used as a source of antibody. This culture supernatant is used to coat the magnetic beads using the procedure described in Example 2. To extract trophoblast cells from the blood of pregnant women, use is made of the ability of the MAb FDO161G, FDO66Q or FDO338P, to bind specifically to trophoblast cells in the maternal blood and not to any other circulating blood-cell. Thus MAbs bind specifically to cells and/or cell fragments which carry the trophoblast membrane proteins defined by each MAb as described above. The beads, with trophoblast cells attached, can then be extracted from the blood cell suspension using a magnet. In an alternative isolation method, the MAbs may be labelled with a fluorescent label, and trophoblast cells bound by the fluorescent-labelled MAbs identified and removed from the sample in a fluorescence-activated cell sorter.

The trophoblast cells isolated by either method can be examined to obtain genetic and/or biochemical information. A number of techniques are known for obtaining genetic information in particular for determining fetal sex and genetic abnormalities. One such technique involves the use of segments of nucleic acid as probes or primers.

Nucleic acid probes are hybridized to the nucleic acid of the isolated trophoblast cells. This method is based on the fact that two complementary strands in a deoxyribonucleic (DNA) double helix can be separated by denaturation and then reannealed (hybridized) under conditions where the hydrogen bonding of base pairs is favoured. Therefore, if the correct complementary nucleic acid sequence is present on the nucleic acid strands of the isolated trophoblast cells, resulting in hybridization of the nucleic acid probe, an appropriate signal can be measured. Since the number of fetal trophoblast cells is very low, a technique of amplifying the signal is desirable. For example, through the use of DNA primers, the polymerase chain reaction, can be used. In this process, the specific nucleic acid sequence targeted through the DNA primers is copied many times by an enzyme, Taq Polymerase. This enables detection of the amplified product by electrophoresis on agarose or polyacrylamide gels. Visualisation of the DNA can be carried out using ultraviolet light after staining with ethidium bromide, or, through detection of radio-labelled product, from radio-labelled nucleotides. Furthermore the isolated trophoblast cells can be useful for biochemical analysis.

To demonstrate the utility of the trophoblast cell isolation from blood using the monoclonal antibodies FDO161G or FDO66Q or FDO338P and the magnetic polystyrene beads, the polymerase chain reaction (PCR) has been used to distinguish between cells of male or female origin. To determine the sensitivity of detection, peripheral blood lymphocytes were used. Using Y chromosome specific primers a signal has been reproducibly obtained from as few as 6 male lymphocytes after 30 amplification cycles of PCR. An equivalent number of female cells taken through the same procedure yields either no detectable amplification product (more common) or a small amount of a slightly smaller sized product readily distinguished from that of male cells.

Blood samples (approx 25ml) were obtained from pregnant women about to undergo chorionic villous biopsy for detection of fetal genetic abnormalities. Fetal trophoblast cells were isolated from the samples using magnetic beads coated with Mab FDO161G or FDO338P as described. The isolated cells attached to the beads were processed through the PCR using the Y-chromosome specific primers. This enabled prediction of the sex of the fetus. Of eleven samples processed, the prediction was confirmed in eleven by routine chromosomal analysis of the chorionic villous sample carried out independently in an unrelated laboratory (P <0.0005). This result demonstrates the utility of the methodology, thus:

1. That the antibodies FDO161G or FDO66Q and FDO338P which define two separate human trophoblast membrane proteins can be employed to isolate fetal cells.

2. That the cells isolated are of fetal origin since male cells were identified in seven cases.

3. That the cells isolated can subsequently undergo procedures which can detect genetic markers with appropriate probes.

Another aspect of this invention is in the detection of genetic abnormalities and/or fetal sex by examination of chromosomes after culture of the isolated cells. For example, this would enable detection of the common genetic disorder, Down's syndrome, for which it is less likely that a genetic probe will become available in the near future.

The cells isolated by the magnetic bead technique can be placed into plastic culture dishes and induced to divide by the addition of growth factors derived from other cultured cells. Preferred cell cultures are those of decidual cells obtained during elective termination of pregnancy, and human granulosa cells obtained during the procedure of egg collection for In Vitro fertilization. Cell free supernatants from these cell cultures are added at a suitable concentration to the isolated trophoblast cell suspensions. Division of cells can be arrested at an appropriate time by the addition of known reagents, e.g. colchicine, then the chromosomes analyzed by standard cytogenetic diagnostic techniques.

The present invention also extends to a kit for the isolation of trophoblast cells from a blood sample of a pregnant mammal and optionally for obtaining genetic and/or biochemical information about said cells comprising in compartmental form a first container adapted to contain an antibody specific for villous syncytiotrophoblast and non-villous cytotrophoblast cells; optionally a second container adapted to receive and contain a blood sample from said pregnant mammal; and optionally a third container adapted to contain a means for obtaining genetic and/or biochemical information from the isolated trophoblast cells.

The antibody in the first container is either a monoclonal antibody or a polyclonal antibody or a combination thereof, and even more preferably FDO161G or FDO66Q or FDO338P and/or combinations thereof. It is a preferred embodiment that the monoclonal antibody is first bound to a substrate such as the magnetic polystyrene beads discussed above.

The following examples describe in detail the production of the monoclonal antibodies to the human trophoblast membrane proteins of this invention and the use of these antibodies to demonstrate the utility of the invention. The methods used in this demonstration are included by way of illustration and not limitation of the subject invention, it being recognized that various modifications are possible within the scope of the invention.

EXAMPLE 1

PRODUCTION OF MONOCLONAL ANTIBODIES a. Preparation of Syncytiotrophoblast

First trimester placentas were obtained from elective terminations of apparently healthy pregnancies performed by aspiration at 6–10 weeks gestation. Clotted blood and any adherent decidua were carefully dissected from the placentas. Syncytiotrophoblast was isolated by gently teasing the placentas through a 250-mesh sieve. The sheets of syncytiotrophoblast, being significantly larger than contaminating cells, readily sediment at unit gravity in Earle's Balanced Salt Solution (Flow Laboratories, Sydney, Australia). After sedimentation for approximately 2 min, the supernatant was decanted and the cells resuspended in fresh solution. This washing procedure was performed three times, then the cells were either used for immunization in mice or placed into culture. The success of trophoblast isolation was confirmed by the synthesis of human chorionic gonadotrophin in culture after three days incubation. Human chorionic gonadotrophin concentration was measured with a solid phase two-site immunoradiometric assay (Hybritech, Calif. USA).

Balb/c mice were immunized intraperitoneally with 0.5ml of trophoblast cell suspension. The immunogen was given at weekly intervals for six weeks following a three week delay after the primary injection.

b. Preparation of choriocarcinoma cell suspension

The choriocarcinoma line, JEG-3, was obtained from the American Type Culture Collection. Cells were cultured in 6-well dishes in RPMI-1640 supplemented with 10% (v/v) heat-inactivated fetal calf serum, L-Glutamine (2 mM), penicillin (100 IU/ml) and streptomycin (100 µg/ml) at 37° C. in a humid atmosphere of 5% $CO_2$ in air. When the cultures were confluent, the cells were scraped from 2 wells, resuspended in 0.5 ml unsupplemented RPMI1640 and injected intraperitoneally. This immunogen was injected intraperitoneally into Balb/c mice at weekly intervals for 6 weeks.

c. Preparation of wheat germ lectin eluate

The wheat germ lectin eluate was prepared using first trimester placenta. Placental membrane proteins were solubilized by the addition of an 8mM solution of 3-[(cholamidopropyl)dimethylammonio]1-propanesulphonate (CHAPS) in 20 mM Tris-HCl, pH 8.0 buffer with 0.02% (w/v) sodium azide, 5 mM Ethylenediaminetetra-acetic acid (EDTA) and 1 mM Phenylmethylsulphonylfluoride (PMSF) in the ratio of 1:10 (w/v). After stirring for 17 hours at 4° C. the insoluble material was removed by centrifugation at 2000 g for fifteen minutes. Wheat Germ Agglutinin covalently linked to agarose beads (approx one ml of packed beads) was incubated batchwise, with stirring for 17 hours, with the solubilized placental preparation (approx 30 ml). The beads were then recovered by centrifugation at 200 g for five minutes and transferred to a column for washing with three volumes of 200 mM N-acetylglucosamine in homogenization buffer. For primary immunization in Balb/c mice, the extract was emulsified with Freund's Complete Adjuvant (1:1, v/v). One half ml of emulsion was injected subcutaneously at several sites into Balb/c mice. Three weeks following the primary immunization, three weekly boosts of 0.5 ml of the extract alone were given intraperitoneally.

d. Fusion of immune mouse spleen cells with myeloma cells

Five days prior to the fusion procedure, mice were injected intraperitoneally with 0.5 ml of Freund's Incomplete Adjuvant. The last boost was administered on the following day. Spleen cells from the immunized mice were fused with mouse myeloma P3x63.Ag8.653 cells. The fusion cell mixture was dispensed initially into 24 hour plates at a spleen cell concentration of $2 \times 10^7$ cells.ml and allowed to grow in the presence of RPMI 1640 (Flow Laboratories) medium containing 10% (v/v) heat-inactivated fetal calf serum (Flow Laboratories), $1 \times 10^{31\ 7}$ aminopterin, $1.6 \times 10^{-5}$ M thymidine, 2 mM L-Glutamine, 100 units/ml penicillin and 100 µg/ml streptomycin at 37° C. in a humid atmosphere of 5% $CO_2$ in air for about 10 days. A few cells from each hybrid colony were then picked out and transferred to individual wells of other 24-well plates. To both minimise the probability of isolating colonies secreting MAbs which identified carbohydrate epitopes and facilitate the possible use of trophoblast-reactive MAbs in immunoaffinity gels, IgG secreting clones were identified using an antigen capture ELISA technique. Briefly, ELISA plates were coated with anti-mouse Ig and the culture supernatant from each hybrid colony added. After adequate incubation time and washing, an IgG class specific enzyme conjugated second antibody was added and developed with the appropriate enzyme substrate. All IgM secreting clones were discarded and the culture supernatants containing IgG or A were screened for antibody binding activity on frozen sections of first trimester placenta using an immunoperoxidase technique (see below). Cultures of interest were then cloned twice by the limiting dilution method and further expanded in culture.

e. Determination of the tissue specificity of monoclonal antibodies by immunoperoxidase staining of frozen sections Sections of frozen tissue were cut at −20° C. using an American Optical Cryostat. Five-µm thick sections were air-dried on chrome-alum gelatin-coated slides for 2 h. The tissue sections were incubated with cell culture supernatants containing antibodies for either 1–2 h at room temperature or overnight at 4° C. Bound antibody was revealed by using biotin-labelled horse antibodies to mouse IgG followed by avidin-biotinylated peroxidase complex (Vector Laboratories, Burlingame, Calif.). Diaminobenzidine (DAB) (0.5 mg/ml) with 0.01% hydrogen peroxide in 20 mM imidazole buffer, pH 7.0, was the enzyme substrate. Sections were counterstained with Mayer's Haemalum. Cover slips were then mounted on air dried sections with DePeX.

For tissues containing substantial amounts of endogenous biotin such as liver and kidney, an indirect immunoperoxidase technique was used. An appropriate dilution of peroxidase-labelled goat anti-mouse IgG reduced the high background staining found with the avidin-peroxidase complex technique.

Human tissues were obtained as follows; first trimester placenta and decidua were obtained from elective pregnancy terminations, term placentas within 1 hr of delivery, and endometrium, myometrium, ovary, cervix, stomach, colon and rectum were obtained at surgery. The remainder were obtained within 6 h postmortem. Tissues were frozen in liquid nitrogen, then stored at −70° C. for less than two months.

A monoclonal antibody (FDO114G) produced in the inventors' laboratory, which reacts with Type IV collagen, acted as a positive control on all tissues.

f. Selection of monoclonal antibodies to human trophoblast membrane protein.

The monoclonal antibodies described in this invention were selected on the basis of the following criteria:

1. They were of the IgG class.
2. The cell lines which secrete the respective antibodies are stable and fast growing in culture, continue to secrete the Mab concerned, can be stored frozen in liquid nitrogen and can be retrieved from the frozen state.
3. The monoclonal antibodies are strongly reactive with human villous syncytotrophoblast end non-villous trophoblast on human placentas throughout pregnancy. They do not react with the mesenchymal cells of the placenta. FDO161G and FDO66Q have very restricted reactivity with other human tissues, FDO338P does not react with any of a large panel of other human tissues tested. None react with human peripheral blood cells or serum components.
4. The protein antigens which these monoclonal antibodies define, viz. FDO161G/FDO66Q protein and FDO338P protein are glycoproteins and hence the epitopes are most likely expressed on the surface membrane of trophoblast cells.

The application of these stringent criteria means that the Mabs selected have the optimal ability to extract trophoblast cells which circulate at very low frequency in maternal blood during pregnancy.

EXAMPLE 2

ISOLATION AND CONFIRMATION OF TROPHOBLAST CELLS FROM MATERNAL BLOOD SAMPLES a. preparation of antibody-coupled substrate The source of each Mab is cell free culture supernatant from the respective cell line cultured in standard conditions (RPMI 1640 medium supplemented with 10% (v/v) heat inactivated fetal calf serum, 2 mM L-Glutamine, 100 units/ml penicillin and 100 µg/ml streptomycin at 37° C. in a humid atmosphere of 5% $CO_2$ in air). The supernatant is collected from well grown cultures, centrifuged to remove cells and stored frozen at −20° C.

The substrate used is a preparation of commercially available, magnetic polystyrene beads precoated with sheep anti-mouse IgG (Fc fragment) serum (Dynabeads M-450, Dynal AS, Oslo, Norway).

One (1) ml of sterile supernatant is mixed with 20 million beads, and the tube rotated end-to-end on a mixer at room temperature. The coated beads are then stored at 4° C. Before use, the beads are washed three times in phosphate-buffered saline containing 1% (v/v) heat-inactivated fetal calf serum (2 min each wash). The beads are collected from the washing solution each time using a cobalt-samarium magnet. The tube is rested on the magnet for a few minutes; allowing the beads to settle on the inner surface of the tube resting on the magnet. The washing solution is aspirated off. The beads are finally resuspended in ice-cold RPMI 1640 culture medium containing L-Glutamine (2 mM) to give approximately $2.5 \times 10^5$ beads/ml.

b. Isolation of trophoblast cells from blood sample

A 25 ml sample of blood is collected from the antecubital vein of a pregnant woman into a syringe containing 10 IU of lithium heparin/ml whole blood. The blood is diluted ten fold with ice-cold RPMI 1640 medium containing 2 mM L-Glutamine, penicillin (100 IU/ml), streptomycin (100 g/ml) and heparin (10 IU/ml), gently mixed, and kept at 4° C. while the beads are being washed as described above. The diluted blood and washed beads are mixed gently (4000 beads/ml whole blood i.e. $10^5$ per 25 ml sample) and incubated at 4° C. overnight. The beads, with trophoblast cells attached via the specific trophoblast reactive antibody, are removed using a cobalt-samarium magnet (Dynal AS). The large volume of the mixture may be processed continuously (by flow over the magnet) or batchwise to remove the beads. In the case of batchwise processing, the volume of the medium containing the beads is finally reduced to 0.4 ml through successive extraction and washing. At this stage, the bead-cell mixtures can either be prepared for DNA sequence amplification or placed into culture.

c. Method for detection of cells containing a Y chromosome

In order to verify that the cells isolated by the beads with bound Mab to trophoblast membrane protein were indeed, fetal in origin, a Y chromosome specific signal was employed to detect the Y chromosome in the isolated cells. The polymerase chain reaction (PCR) was used since the cells are present in very low numbers. The male specific signal has been obtained using a pair of DNA primers to a Y chromosome repeat sequence. The primer pair which was found to give satisfactory specificity and signal strength was designated WYR7 and WYR8. The size of the amplified DNA sequence is 124 base pairs (bp). The sequence of the primers are as follows:

WYR7 5' TGG GCT GGA ATG GAA AGG AAT CGA AAC 3'

WYR8 5' TCC ATT CGA TTC CAT TTT TTT CGA GAA 3'

The protocol used has been as follows:

1. Cells bound to magnetic beads were aliquoted into 0.5 ml Eppendorf tubes in saline. The volume of saline has been minimised although for 25 µl of PCR buffer mixture, the reaction is tolerant of saline up to a volume of at least 10 µl.

2. Cells in saline have been lysed by heating in a water-bath at 100° C. for 10 min. The cell suspension is covered by a layer of paraffin oil and the tube is capped during this process.

3. PCR buffer is then added (to 25 µl). The final concentration of regents in the reaction mixture are: 67 mM Tris-HCl (pH 8.8 at 25° C.), 2.0 mM $MgCl_2$, 0.01% (w/v) gelatin, 10 mM β-mercaptoethanol, 16.6 mM ammonium sulfate, 17 µg/ml bovine serum albumin, 10% dimethyl sulfoxide, 0.1 mM deoxynucleotide triphosphates, 0.25 µg of each primer and 0.2 units of Taq DNA polymerase (Thermophilus aquaticus).

4. 30 cycles of PCR are then carried out as follows:

| | |
|---|---|
| Denaturation step | 94° C. for 1 min |
| Annealing step | 55° C. for 1 min |
| Polymerase extension step | 72° C. for 1 min |

Each round of amplification is the same except that (i) the first denaturing step is for a period of 6 min., (ii) extension time of the final cycle is 10 min.

5. The PCR product is electrophoresed in agarose or polyacrylamide gels by standard methods and visualized under ultraviolet light after the gel has been stained with ethidium bromide.

Trophoblast cells bound to magnetic beads have been accurately quantified by microscopy and a Y chromosome specific signal can be reproducibly obtained from only 6 male lymphocytes after 30 cycles of the PCR. An equivalent number of female cells taken through the same PCR yields no detectable signal or an exceedingly weak signal readily distinguished from that of male cells.

The signals obtained from control trophoblast cells derived from a full-term placenta of a male child and CVS confirmed male and female fetal cells isolated by Mab coated beads are demonstrated in FIG. 1. The inventor's laboratory has processed eleven blood samples from pregnant women undergoing chorionic villous sampling biopsy. The predicted sex of the fetus was confirmed in eleven out of eleven cases (P <0.0005).

d. Culture of isolated fetal trophoblast cells

Trophoblast cells, with beads attached are placed into 48 well plastic culture dishes with coverslips in the base of the dishes and covered with a complex culture medium comprising a 1:1:1 mixture of (a) culture supernatant from human decidual cells obtained from elective termination of early pregnancy, (b) culture supernatant from human granulosa cells (obtained during the procedure of egg collection in an In Vitro fertilization programme) and (c) standard culture medium RPMI 1640 containing 10% (v/v) normal human female serum, 2 mM L-Glutamine, 100 units/ml penicillin and 100 µg/ml streptomycin) at 37° C. in a humid atmosphere of 5% $CO_2$ in air. After 14–21 days culture, the trophoblast cell cultures have reached sufficient cell density to perform chromosome studies. This is done by standard techniques performed in cytogenetic diagnosis. The culture supernatants (a) and (b) (above) were obtained from cultures of decidual cells and granulosa cells in standard medium; the culture supernatant was collected, centrifuged to remove cells and stored at −20° C.

Hybridomas FDO66Q (ATCC HB 11569), FDO338P (ATCC HB 11570), and FDO161G (ATCC HB 11571) were each deposited with the American Type Culture Collection, 12301 Parklawn Drive, Rockville, Md. 20852 on Mar. 10, 1994.

REFERENCES:

1. Adinolfi, M. et al. (1989) *Lancet* 2, 328
2. Anderson, D. J. et al. (1987) *J. Reprod. Immunol* 10,231.
3. Covone, A. E. et al. (1984) *Lancet* 2,841.
4. Goodfellow, C. F. & Taylor, P.V. (1982) *Brit. J. Obstet. Gynaecol.* 89,85.
5. Johnson, P. M. et al. (1981) *Am. J. Reprod. Immunol.* 1,246.
6. Lipinski, M. et al. (1981) *Proc. Natl. Acad. Sci. (USA)* 78,5147.
7. Loke, Y. W. & Day, S. (1984) *Am J. Reprod. Immunol.* 5,106.
8. Mueller, U. W. et al. (1987) *Histochemical J.* 19,288.
9. Pool, C. et al. (1987) *Lancet* 1,804.
10. Schwinger, E. et al. (1989) *Am. J. Human Genetics* 45,1057 (abstract).
11. Sunderland, C. A. et al. (1981) *Immunology* 45,541.

We claim:

1. A method for the isolation of trophoblast cells from a peripheral blood sample of a pregnant mammal, which method comprises contacting said blood sample with a at least one monoclonal antibody that specifically binds an epitope of a trophoblast membrane protein resident on villous syncytiotrophoblast and non-villous cytotrophoblast cells but which does not delectably bind to any other blood-borne cells of maternal or fetal origin, for a time and under conditions sufficient for said at least one antibody to specifically bind said trophoblast cells, and then separating said trophoblast cells bound by said antibody from said sample.

2. The method according to claim 1 wherein said mammal is a human female.

3. The method according to claim 1 wherein the protein is a surface-expressed trophoblast membrane protein which migrates on sodium dodecyl-sulphate polyacrylamide gel electrophoresis as a series of molecular weight entities ranging from 30 kDa to 67 kDa.

4. The method according to claim 1 wherein the protein is a glycoprotein and has no N-linked high mannose chains but has between 3 and 6 O-linked and between 5 and 10 complex N-linked oligosaccharide chains per molecule or in which the glycoprotein has no N-linked but between 3 and 6 O-linked oligosaccharide chains per molecule.

5. The method according to claim 4 wherein the protein has a molecular weight of about 43kDa, an N-terminal sequence of Thr-Gly-Trp-Ser-His-Leu-Val-Thr-Gly-Ala-Gly-Gly-Phe-Leu-Gly-Gln-(Y)-Ile-(Y)-(Y)-Leu-(Y)-Val-Lys-(Y), end a partial internal sequence of -Phe-(X)-Leu-Arg-Leu-Glu-Ser-Arg-(X)-Ser-Phe-Pro-Leu-(Y)-(X)-Met-Tyr-(X)-Ile-, wherein X represents Ser or Thr and Y represents an unknown amino acid.

6. The method according to claim 1 wherein the antibody is produced by hybridoma ATCC HB 11569, hybridoma ATCC HB 11570, or hybridoma ATCC HB 11571 or any combination thereof.

7. The method according to claim 1 wherein said at least one antibody is immobilized on a solid substrate.

8. A method according to claim 7 wherein the solid substrate comprises magnetic beads.

9. The method according to claim 8 wherein the substrate comprises magnetic polystyrene beads precoated with sheep anti-mouse IgG Fc Fragments serum.

10. The method according to claim 8, wherein the separation of cells bound by antibody from the sample comprises the step of continuously passing the sample past a magnet.

11. The method according to claim 1 wherein said at least one antibody is first conjugated to a fluorescent label.

12. The method according to claim 11, wherein the fluorescent label is one suitable for use in fluorescence-activated cell sorting.

* * * * *